United States Patent
Noda

(10) Patent No.: US 7,393,911 B2
(45) Date of Patent: Jul. 1, 2008

(54) ORGANOSILICON FINE PARTICLES AND METHOD OF PRODUCING SAME

(75) Inventor: Ippei Noda, Gamagori (JP)

(73) Assignee: Takemoto Yushi Kabushiki Kaisha, Aichi (JP)

( * ) Notice: Subject to any disclaimer, the term of this patent is extended or adjusted under 35 U.S.C. 154(b) by 486 days.

(21) Appl. No.: 11/061,961

(22) Filed: Feb. 17, 2005

(65) Prior Publication Data

US 2006/0089478 A1 Apr. 27, 2006

(30) Foreign Application Priority Data

Oct. 25, 2004 (JP) ............... 2004-309310

(51) Int. Cl.
*C08L 83/04* (2006.01)
*A61K 31/695* (2006.01)
*C08G 77/08* (2006.01)

(52) U.S. Cl. ................. 528/10; 528/34; 424/78.02

(58) Field of Classification Search .............. 528/10, 528/34; 424/78.02
See application file for complete search history.

(56) References Cited

U.S. PATENT DOCUMENTS

| 5,352,645 | A | * | 10/1994 | Schwartz | 502/262 |
|---|---|---|---|---|---|
| 6,045,904 | A | * | 4/2000 | Torikoshi et al. | 428/334 |
| 2002/0193463 | A1 | * | 12/2002 | Jones et al. | 523/115 |
| 2005/0020699 | A1 | * | 1/2005 | Isobe et al. | 516/33 |
| 2005/0256222 | A1 | * | 11/2005 | Jones et al. | 523/116 |

FOREIGN PATENT DOCUMENTS

WO WO 03/055799 * 10/2003

OTHER PUBLICATIONS

Noda, Ippei and Akira Nakamura, Chemistry of Materials, 2001, 16, 3579-3581.*
Iskandar et al. Journal of Nanoparticle Research, 2001, 3, 263-270.*
Patwardhan et al. Silicon Chemistry, 2002, 1, 47-55.*

* cited by examiner

*Primary Examiner*—Randy Gulakowski
*Assistant Examiner*—Robert Loewe
(74) *Attorney, Agent, or Firm*—Weaver Austin Villeneuve & Sampson LLP

(57) ABSTRACT

Organosilicon fine particles with polysiloxane network structure made of siloxane units of specified kinds at specified ratios and having a circular ring shape as a whole and average outer and inner diameters within specified ranges such that their difference is also within a specified range can provide antireflection and antiblocking characteristics to synthetic polymer films and sheets when applied to their surface or caused to be contained, respectively, and adherence and slip characteristics to a skin care cosmetic material when caused to be contained.

10 Claims, No Drawings

ORGANOSILICON FINE PARTICLES AND METHOD OF PRODUCING SAME

Priority is claimed on Japanese Patent Application 2004-309310 filed Oct. 25, 2004.

BACKGROUND OF THE INVENTION

This invention relates to organosilicon fine particles having a new shape and a method of producing such organosilicon fine particles, as well as polymer modifiers and cosmetic materials comprising such organosilicon fine particles.

Organosilicon fine particles comprising polysiloxane network structures are widely being used as polymer modifiers, cosmetic materials, coating materials, diagnostic agent carriers and paint materials. This invention relates to such organosilicon fine particles having a circular ring shape as a whole.

Examples of such organosilicon fine particles which have conventionally been known include (1) those that are solid and spherical with smooth surface (such as disclosed in U.S. Pat. Nos. 4,652,618 and 4,892,726 and Japanese Patent Publications Tokkai 61-159467, 61-194009, 63-15849, 63-8461, 63-77940, 63-312324, 1-144423, 2-209927, 4-337390, 6-279589 and 6-49209); (2) those that have many indentations on the surface and are solid and spherical as a whole (such as disclosed in Japanese Patent Publication Tokkai 2000-191788); (3) those that are sectionally horseshoe-shaped (such as disclosed in Japanese Patent Publication Tokkai 2000-191789); (4) those that are hollow and semispherically shaped (such as disclosed in Japanese Patent Publication Tokkai 2003-128788); and (5) those in the shape of a rugby ball (such as disclosed in Japanese Patent Publication Tokkai 2003-171465). These prior art organosilicon fine particles are noted as polymer modifiers and cosmetic materials because of their lubricity, non-stickiness, oil-absorbing property, dispersibility, heat-resistance, resistance against solvents and water repellency.

These prior art organosilicon fine particles have problems, however, when used as a polymer modifier or a cosmetic material because they are not sufficiently effective for the purpose. When such prior art organosilicon fine particles are used as an antireflection agent for an antireflection film of a liquid crystal display, for example, there is the problem that the product turns out to be inferior in antireflection property and clarity of transmitted image. If they are used as an anti-blocking agent for a polymer film, as another example, there is the problem that the product turns out to be inferior in adherence resistance and anti-slip. If they are used as a cosmetic material for a skin care, furthermore, there is the problem that they are inferior in stickiness and slip.

SUMMARY OF THE INVENTION

It is therefore an object of this invention to provide organosilicon fine particles capable of being used as a polymer modifier or a cosmetic material by showing results desired for the purposes of their use.

The invention is based on the discovery by the present inventors as a result of their diligent work in view of the aforementioned object that organosilicon particles comprising polysiloxane network structures having a circular ring shape as a whole with a specified size are appropriate for the purpose of this invention.

The invention relates to organosilicon fine particles comprising polysiloxane network structure having a circular ring shape as a whole, having an average outer diameter of 0.05-15 μm and an average inner diameter of 0.0-10 μm, wherein the difference between the average outer diameter and the average inner diameter is in the range of 0.04-5 μm. The invention also relates to a method of producing such organosilicon fine particles as well as polymer modifiers and cosmetic materials comprising such organosilicon fine particles.

The organosilicon fine particles according to this invention will be described first. The organosilicon fine particles according to this invention are characterized as comprising polysiloxane network structure which is a three-dimensional network structure of siloxane units. The invention does not impose any particular limitations on the kinds or ratios of these siloxane units that comprise the polysiloxane network but siloxane units given respectively by Formulas (1), (2), (3), (4), (5) and (6) shown below and satisfying the three conditions described below simultaneously are preferred:

| | |
|---|---|
| $SiO_{4/2}$ | Formula (1) |
| $Si(OH)O_{3/2}$ | Formula (2) |
| $R^1 SiO_{3/2}$ | Formula (3) |
| $R^2 SiO_{3/2}$ | Formula (4) |
| $R^3 Si(OH)O_{2/2}$ | Formula (5) |
| $R^4 Si(OH)O_{2/2}$ | Formula (6) | where $R^1$ and $R^3$ are each nonreactive hydrocarbon group, and $R^2$ and $R^4$ are each organic group having reactive group selected from the group consisting of acryloxy group, methacryloxy group, vinyl group and mercapto group, and where the aforementioned three conditions are (1) the molar ratio of (siloxane unit shown by Formula (1))/(siloxane units shown by Formulas (2), (3), (4), (5) and (6))=20/80-50/50; the molar ratio of (siloxane units shown by Formulas (2), (3) and (4))/(siloxane units shown by Formulas (5) and (6))=50/50-75/25; and (3) the molar ratio of (siloxane units shown by Formulas (3) and (5))/(siloxane units shown by Formulas (4) and (6))=20/80-60/40.

Siloxane unit shown by Formula (1) is silica unit. Siloxane unit shown by Formula (2) is hydroxysiloxane unit.

In Formula (3), $R^1$ stands for a nonreactive hydrocarbon group. Examples of such nonreactive hydrocarbon group include alkyl groups, cycloalkyl groups, aryl group, alkylaryl group and aralkyl group. Out of these examples, alkyl groups with 1-3 carbon atoms such as methyl group, ethyl group and propyl group are preferable and methyl group is particularly preferable. Examples of siloxane unit shown by Formula (3) include methylsiloxane unit, ethylsiloxane unit and propylsiloxane unit but methylsiloxane unit is preferable.

In Formula (4), $R^2$ stands for an organic group having a specified reactive group. Examples of such specified reactive group include acryloxy group, methacryloxy group, vinyl group and mercapto group. Examples of organic group having such reactive group include (1) organic groups having acryloxy group such as 2-acryloxy ethyl group and 3-acryloxypropyl group; (2) organic groups having methacryloxy group such as 2-methacryloxyethyl group and 3-methacryloxypropyl group; (3) organic groups having vinyl group such as vinyl group, allyl group, isopropenyl group and 2-methylallyl group; and (4) organic groups having mercapto group such as mercaptopropyl group and mercaptoethyl group. Examples of siloxane unit shown by Formula (4) include (1) siloxane units having acryloxy group such as 2-acryloxyethylsiloxane and 3-acryloxypropylsiloxane; (2) siloxane units having methacryloxy group such as 2-methacyloxyethylsiloxane unit and 3-methacryloxypropylsiloxane unit; (3) siloxane units having vinyl group such as vinylsiloxane unit, allylsiloxane unit and isopropenylsiloxane unit; and (4) siloxane units having mercapto group such as mercaptopropylsiloxane unit and mercaptoethylsiloxane unit. Among the above, however, siloxane units having acryloxy group and siloxane units having methacryloxy group are preferable.

In Formula (5), $R^3$ is as described for $R^1$ of Formula (3). Examples of siloxane unit shown by Formula (5) include hydroxymethylsiloxane unit, hydroxyethylsiloxane unit and hydroxypropylsiloxane unit. Among the above, hydroxymethylsiloxane is preferable.

In Formula (6), $R^4$ is as described for $R^2$ of Formula (4). Examples of siloxane unit shown by Formula (6) include (1) hydroxysiloxane units having acryloxy group such as hydroxy-2-acryloxyethylsiloxane unit and hydroxy-3-acryloxypropylsiloxane; (2) hydroxysiloxane units having methacryloxy group such as hydroxy-2-methacryloxyethylsiloxane unit and hydroxy-3-methacryloxypropylsiloxane; (3) hydroxysiloxane units having vinyl group such as hydroxyvinylsiloxane unit, hydroxy-allylsiloxane unit and hydroxy-isopropenylsiloxane unit; and (4) hydroxysiloxane units having mercapto group such as hydroxy-mercaptopropylsiloxane unit and hydroxy-mercaptoethylsiloxane unit. Among the above, hydroxysiloxane units with acryloxy group and hydroxysiloxane units with methacryloxy group are preferable.

When the polysiloxane network structure of this invention is formed with siloxane units as described above, the molar ratios among these siloxane units are selected so as to satisfy the aforementioned three conditions. The first of the conditions requires that the molar ratio of (siloxane unit shown by Formula (1))/(siloxane units shown by Formulas (2), (3), (4), (5) and (6))=20/80-50/50 but it is preferable that this molar ratio be within the range of 25/75-45/55. The second condition requires that the molar ratio of (siloxane units shown by Formulas (2), (3) and (4))/(siloxane units shown by Formulas (5) and (6))=50/50-75/25 but it is preferable that this molar ratio be within the range of 60/40-70/30. The third condition requires that the molar ratio of (siloxane units shown by Formulas (3) and (5))/(siloxane units shown by Formulas (4) and (6))=20/80-60/40 but it is preferable that this molar ratio be within the range of 25/75-45/55.

Organosilicon fine particles of this invention comprise polysiloxane network structure as described above and have a circular ring shape as a whole. Their average outer diameter is 0.05-15 μm and average inner diameter is 0.01-10 μm such that the difference between the average outer diameter and the average inner diameter is in the range of 0.04-5 μm. It is preferable, however, that the average outer diameter is 0.1-8 μm and the average inner diameter is 0.05-6 μm such that their difference is 0.5-3 μm. These average values are both obtained by using a scanning electron microscope to measure inner and outer diameters of arbitrarily selected 100 samples extracted from a secondary electron image and taking their averages.

Next, a method of producing organosilicon fine particles embodying this invention will be described. This will be a method of producing the organosilicon fine particles as described above and comprises the steps of using silanol group forming silicides given respectively by Formulas (7), (8) and (9) shown below:

$SiX_4$  Formula (7)

$R^5SiY_3$  Formula (8)

$R^6SiZ_3$  Formula (9)

where $R^5$ is nonreactive hydrocarbon group, $R^6$ is organic group having reactive group selected from the group consisting of acryloxy group, methacryloxy group, vinyl group and mercapto group, and X, Y and Z are each alkoxy group with 1-4 carbon atoms, alkoxyethoxy group having alkoxy group with 1-4 carbon atoms, acyloxy group with 2-4 carbon atoms, N,N-dialkylamino group having alkyl group with 1-4 carbon atoms, hydroxyl group, halogen atom or hydrogen atom, said silanol group forming silicides being used such that molar ratio of (silanol group forming silicide of Formula (7))/((silanol group forming silicide of Formula (8))+(silanol group forming silicide of Formula (9))=25/75-60/40 and molar ratio of (silanol group forming silicide of Formula (8))/(silanol group forming silicide of Formula (9))=20/80-60/40, generating silanol compounds by causing such silanol group forming silicides to contact with water in the presence of a catalyst and to thereby undergo hydrolysis, and causing a condensation reaction of these silanol compounds to thereby generate the organosilicon fine particles comprising polysiloxane network structure.

In the above, silanol group forming silicide given by Formula (7) is a compound that eventually forms siloxane units given by Formulas (1) and (2) and X in Formula (7) is (1) alkoxy group with 1-4 carbon atoms such as methoxy group and ethoxy group; (2) alkoxyethoxy group having alkoxy group with 1-4 carbon atoms such as methoxy group, ethoxy group and butoxyethoxy group; (3) acyloxy group with 2-4 carbon atoms such as acetoxy group and propyoxy group; (4) N,N-dialkylamino group having alkyl group with 1-4 carbon atoms such as dimethylamino group and diethylamino group; (5) hydroxyl group; (6) halogen atom such as chlorine atom and bromine atom; or (7) hydrogen atom.

Examples of silanol group forming silicide shown by Formula (7) include tetramethoxy silane, tetraethoxy silane, tetrabutoxy silane, trimethoxyethoxy silane, tributoxyethoxy silane, tetraacetoxy silane, tetrapropyoxy silane, tetraacetoxy silane, tetra(dimethylamino) silane, tetra(diethylamino) silane, tetrahydroxy silane, chloro-silane triol, dichloro-disilanol, tetrachloro-silane and chloro-trihydrogen silane. Among the above, tetramethoxy silane, tetraethoxy silane, tetrabutoxy silane and tetrapropyoxy silane are preferable.

Silanol group forming silicide given by Formula (8) is a compound that eventually forms siloxane units given by Formulas (3) and (5) and $R^5$ in Formula (8) is as described above for $R^1$ in Formula (3) and Y in Formula (8) is as described above for X in Formula (7).

Examples of silanol group forming silicide shown by Formula (8) include methyltrimethoxy silane, ethyltriethoxy silane, propyltributoxy silane, butyltributoxy silane, phenyltrimethoxy silane, methyltributoxy silane, methyltriacetoxy silane, methyltripropyoxy silane, methyltriacetoxy silane, methyltri(dimethylamino) silane, methyltri(dimethylamino) silane, methylsilane triol, methylchloro disilanol, methyltrichloro silane and methyltrihydrogen silane. Among these, silanol group forming silicides that eventually form methylsiloxane units are preferable, as described above regarding $R^1$ in Formula (3). Silanol group forming silicides that eventually form hydroxymethylsiloxane unit are also preferable, as described above regarding $R^3$ in Formula (5).

Silanol group forming silicide given by Formula (9) is a compound that eventually forms siloxane units given by Formulas (4) and (6) and $R^6$ in Formula (9) is as described above for $R^2$ in Formula (4) and Z in Formula (9) is as described above for X in Formula (7).

Examples of silanol group forming silicide shown by Formula (9) include (1) silane compounds having acryloxy group such as 2-acryloxyethyltrimethoxy silane and 3-acryloxypropyltrimethoxy silane; (2) silane compounds having methacryloxy group such as 2-methacryloxyethyltrimethoxy silane and 3-methacroxypropyltrimethoxy silane; (3) silane compounds having vinyl group such as vinyltrimethoxy silane, allyltrimethoxy silane and isopropenyltrimethoxy silane; and (4) silane compounds having mercapto group such as mercaptopropylmethoxy silane and mercaptoethyltrimethoxy silane. Among the above, silane compounds having acryloxy group and silane compounds having methacryloxy group are preferable.

The present invention further relates to a method of producing organosilicon fine particles of this invention, characterized as comprising the steps of using silanol group forming silicides given respectively by Formulas (7), (8) and (9) shown above, the silanol group forming silicides being used such that molar ratio of (silanol group forming silicide of Formula (7))/((silanol group forming silicide of Formula (8))+(silanol group forming silicide of Formula (9))=25/75-60/40 or preferably 30/70-55/45 and molar ratio of (silanol group forming silicide of Formula (8))/(silanol group forming silicide of Formula (9))=20/80-60/40 or preferably 25/75-45/55, generating silanol compounds by causing the silanol group forming silicides to contact with water in the presence of a catalyst and to thereby undergo hydrolysis. Conventionally known kinds of catalyst for the hydrolysis of silanol group forming silicides may be used. Examples of such catalyst include basic catalysts including inorganic bases such as sodium hydroxide, potassium hydroxide, sodium carbonate, sodium bicarbonate and ammonia and organic bases such as trimethylamine, triethylamine, tetraethyl ammonium hydroxide, dodecyl dimethyl hydroxyethyl ammonium hydroxide and sodium methoxyd, and acidic catalysts including inorganic acids such as hydrochloric acid, sulfuric acid and phosphoric acid and inorganic acids such as acetic acid, citric acid, methane sulfonic acid, p-toluene sulfonic acid, dodecylbenzene sulfonic acid and dodecyl sulfonic acid.

At the time of the hydrolysis by causing silanol group forming silicides of Formulas (7), (8) and (9) to contact with water in the presence of a catalyst, these silanol group forming silicides are usually mixed with water and the catalyst together and stirred and the time when the silanol group forming silicides which are not soluble in water disappear from the reaction system is considered as the end of the hydrolysis. These silanol group forming silicides are different not only regarding their natural ability of hydrolysis, depending on their kinds, but also regarding their ability of hydrolysis based on the difference in their dispersion characteristics in water. Thus, the kind of the catalysis to be used, the amount to be used and the reaction temperature are appropriately selected. In order to make the contact reaction of these silanol group forming silicides with water easier, a surfactant may also be added to the reaction system.

The surfactant to be added to the reaction system together with a catalysis in the production method of this invention is nonion surfactant and/or anion surfactant. Examples of non-ion catalyst include polyoxyalkylene alkylether, polyoxyalkylene alkylphenylether, polyoxyalkylene alkylester and castor oil polyoxyalkylene adduct, all with polyoxyalkylene group formed by a repetition of oxyethylene and/or oxypropylene units. Such a nonion surfactant is preferably added to the reaction system at a concentration of 0.001-0.05 weight %.

Examples of anion surfactant include organic sulfates with 8-18 carbon atoms such as octyl sulfate, cetyl sulfate and lauryl sulfate and organic sulfonates with 8-30 carbon atoms such as octyl sulfonate, cetyl sulfonate, lauryl sulfonate, stearyl sulfonate, oleyl sulfonate, p-toluene sulfonate, dodecylbenzene sulfonate, oleylbenzene sulfonate, naphthyl sulfonate and diisopropylnaphthyl sulfonate. Such an anion surfactant is preferably added to the reaction system at a concentration of 0.005-0.55 weight %.

The weight ratio at which water and the whole of silanol group forming silicides are mixed is usually 10/90-70/30. The amount of the catalyst to be used depends on the kind of the catalyst and the kind of the silanol group forming silicide but it is usually preferable to make it less than 1 weight % against the whole of the silanol group forming silicides. The reaction temperature is usually 0-40° C. but it is preferable to make it below 30° C. in order to avoid instantaneous condensation polymerization reaction of the silanol compounds generated by the hydrolysis.

Silanol group forming silicides of Formulas (7), (8) and (9) may be added into water either all at once for hydrolysis or sequentially while hydrolysis takes place. If the speed of hydrolysis varies significantly among the silanol group forming silicides being used, it is preferable to preliminarily start the hydrolysis of silanol group forming silicide with a slow speed of hydrolysis and then to continue the hydrolysis by subsequently adding the silanol group forming silicides with high speeds of hydrolysis.

In the method of this invention for producing organosilicon fine particles, the silanol compounds obtained by hydrolysis are caused next to undergo a condensation reaction so as to generate organosilicon fine particles made of polysiloxane network structures. The reaction liquid containing the silanol compounds generated by the hydrolysis may be directly used for the condensation reaction or after a catalysis is further added. The reaction temperature at the time of the condensation reaction is usually 0-50° C. but it is preferable to start the condensation reaction at below 30° C. and then to increase the temperature to 30-50° C. thereafter for the condensation reaction. This is how organosilicon fine particles of this invention are obtained in the form of their aqueous suspension.

Organosilicon fine particles of this invention are obtained by separating them from this aqueous suspension and drying them. For example, this aqueous suspension may be passed through a metal net and dehydrated by a centrifugal separation or high-pressure filtering method and the dehydrated object may be heated and dried at 100-250° C. or may be directly heated and dried at 100-250° C. by means of a spray drier. Such a dried object is preferably disorganized, for example, by using a jet mill. If this aqueous suspension is fractionated by means of a porous membrane in the process of obtaining hydrates therefrom, organosilicon fine particles with a reduced fluctuation in sizes can be obtained. Examples of such porous membrane includes porous ceramic membranes produced by a phase separation method, polymer membrane filters made by a phase transition method or a drawing method, cartridge filters produced by winding a polymer drawing thread and pore filters obtained by neutron irradiation but polymer membrane filters are preferred.

Organosilicon fine particles thus obtained have a circular ring shape as a whole, the average of the outer diameter being 0.05-15 μm, the average of the inner diameter being 0.01-10 μm, and the difference between these two average values being within the range of 0.04-5 μm. If a polymer membrane filter is used to fractionate the aqueous suspension of organosilicon fine particles obtained by the condensation reaction of silanol compounds, as explained above, organosilicon fine particles with an average outer diameter of 0.1-8 μm, an average inner diameter of 0.05-6 μm and the difference therebetween of 0.5-3 μm can be obtained.

Organosilicon fine particles of this invention and organosilicon fine particles produced by a method of this invention are widely usable as a polymer modifier, a cosmetic material, a coating material, a diagnostic agent carrier and a paint material and are particularly useful as a polymer modifier and a cosmetic material.

Polymer modifiers according to this invention are characterized as comprising organosilicon fine particles of this invention as described above or organosilicon fine particles produced by a method of this invention and serve to provide a special optical characteristic and adherence resistance to the polymer material surface. Examples of polymer material to which polymer modifiers of this invention may be applied include synthetic polymer films and sheets made of a polymer material such as polyester, nylon, polypropylene, polycaprolactone and acryl resins. Polymer modifiers of this invention are particularly useful when applied as an antireflection agent and an antiblocking agent for synthetic polymer films and sheets.

One of methods for using polymer modifier of this invention as an antireflection agent for a synthetic polymer film or sheet is to paint the synthetic polymer film or sheet with organosilicon fine particles. By this method, an aqueous suspension of organosilicon fine particles is prepared and this is painted over the surface of the synthetic polymer film or sheet by a known method such as the roller touch method or the spray method. The process may be during the step before the stretch orientation immediately after the molten extrusion, the step before the biaxial stretching orientation after the uniaxial drawing orientation or the step before the biaxial stretching orientation in the production process of synthetic polymer films and sheets but it is preferable to be done before the biaxial stretching orientation after the uniaxial drawing orientation. In whatever process, the painting process is carried out such that organosilicon fine particles are applied at the rate of 0.01-0.2 g per 1 $m^2$ of synthetic polymer film or sheet.

Methods of using polymer modifier of this invention as an antiblocking agent for a synthetic polymer film or sheet include: (1) method of causing organosilicon fine particles to be contained by synthetic polymer and then molding into a film or a sheet; and (2) method of painting the synthetic polymer film or sheet with organosilicon fine particles. By the method of (1) above, organosilicon fine particles are made to be contained at a rate of 0.01-5 weight parts or preferably 0.05-3 weight parts per 100 weight parts of synthetic polymer to be molded into a film or a sheet. The invention does not impose any limitation on the method of causing organosilicon fine particles to be contained by synthetic polymer or the method of melting synthetic polymer containing organosilicon fine particles to mold it into a film or a sheet. Any conventionally known method may be used. By the method of (2) above, an aqueous suspension of organosilicon fine particles is prepared and applied onto the surface of a synthetic polymer film or sheet by a conventionally known method such as the roller touch method or the spray method. The painting process may be during the step before the stretch orientation immediately after the molten extrusion, the step before the biaxial stretching orientation after the uniaxial drawing orientation or the step before the biaxial stretching orientation in the production process of synthetic polymer films and sheets but it is preferable to be done before the biaxial stretching orientation after the uniaxial drawing orientation. In whatever process, the painting process is carried out such that organosilicon fine particles are applied at the rate of 0.01-0.2 g per 1 $m^2$ of synthetic polymer film or sheet.

Cosmetic materials of this invention are characterized as comprising organosilicon fine particles of this invention or organosilicon fine particles produced by a method of this invention. Cosmetic materials of this invention may be used as powder materials for skin care such as facial cosmetics, makeup cosmetics, body cosmetics and deodorant, hair cosmetics, oral hygiene articles, bath additives and fragrance but are particularly useful as a skin care because of their adaptability to a variety of sensitivity to use on the skin and to high and multiple functionality as internal capsules and by adsorption of liquid cosmetics components, ultraviolet absorbent, inorganic powder and pigments. When they are used as cosmetic materials, the amount of organosilicon fine particles to be used must be appropriately selected, depending on the manner of use. In the case of makeup cosmetics, for example, it is preferably 1.0-50 weight % for press state makeup cosmetics and 0.1-30 weight % for liquid makeup cosmetics.

When use is made as makeup cosmetic, examples of other material to be used together with organosilicon fine particles include pigment powder, combination oils, water, surfactants, thickeners, antiseptics and perfumes. Makeup cosmetics using these materials can be produced by any conventionally known method of dispersing organosilicon fine particles and such other material uniformly.

As explained above, the present invention has the merit of being able to provide new organosilicon fine particles comprising polysiloxane network structure that are useful as polymer modifier and cosmetic materials.

DETAILED DESCRIPTION OF EMBODIMENTS

Next, the invention is described by way of examples but these examples are not intended to limit the scope of the invention. In what follows, "part" means weight part and "%" means weight %.

Part 1 (Synthesis of Organosilicon Fine Particles)

Test Example 1

Synthesis of Organosilicon Fine Particles (P-1)

Ion exchange water 700 g was placed inside a reactor and 48% aqueous solution of sodium hydroxide 0.3 g was added to prepare an aqueous solution. Methyltrimethoxy silane 32.6 g (0.24 mol), 3-methacryloxypropyl trimethoxy silane 89.3 g (0.36 mol) and tetraethoxy silane 83.2 g (0.4 mol) were added to this aqueous solution for hydrolysis for one hour by keeping the temperature at 13-15° C. to obtain a transparent reaction liquid containing silanol compound. After 10% aqueous solution of dodecylbenzene sodium sulfonate 3 g was added to this reaction liquid, a condensation reaction was carried out for 3 hours by keeping the temperature at 13-15° C. and a further condensation reaction was carried out for 5 hours by keeping the temperature at 30-50° C. to obtain aqueous suspension containing organosilicon fine particles. After this aqueous suspension was passed through a membrane filter with hole diameter of 10 μm produced by Advantec Mfs, Inc., white fine particles were filtered out by means of a centrifuge. The white fine particles thus obtained were washed with water and dried with hot wind for 5 hours at 150° C. to obtain organosilicon fine particles (P-1) 60.1 g. Analyses were carried out by observation with a scanning electron microscope, $^{29}$SiCP/MAS-NMR spectroscopy, elemental analysis, inductive coupled plasma spectroscopy and FT-IR spectroscopy and it was ascertained that organosilicon fine particles (P-1) have a circular ring shape with average outer diameter of 3.0 μm, average inner diameter of 2.2 μm and a difference of 0.8 μm between the average outer diameter and the average inner diameter, and comprising siloxane network structure containing siloxane unit shown by Formula (1) and siloxane units shown by Formulas (2), (3), (4), (5) and (6) at a molar ratio of 32/68, containing siloxane units shown by Formulas (2), (3) and (4) and siloxane units shown by Formulas (5) and (6) at molar ratio of 66/34 and containing siloxane units shown by Formulas (3) and (5) and siloxane units shown by Formulas (4) and (6) at molar ratio of 40/60.

The shape and the average outer and inner diameters of organosilicon fine particles (P-1) were measured by using a scanning electron microscope to observe arbitrarily selected 100 particles at 5000-10000 times and to measure various parts for taking averages. Analysis of binding organic groups was made by accurately measuring 5 g of organosilicon fine particles (P-1), adding it to 0.05N aqueous solution of sodium hydroxide 250 ml and extracting all hydrolytic groups in organosilicon fine particles into the aqueous solution. Organosilicon fine particles were separated from the aqueous solution with an ultracentrifuge and after the separated organosilicon fine particles were washed with water, they were dried for 5 hours at 200° C. and subjected to elemental analysis, ICP emission spectral analysis and FT-IR spectroscopy to measure the total carbon content and silicon content and to ascertain silicon-carbon bonds and silicon-oxygen-silicon bonds. From the results of these analyses, the number of carbon atoms in $R^5$ of the silanol group forming silicide shown by Formula (8) used as the material, the number of carbon atoms in $R^6$ of the silanol group forming silicide shown by Formula (9) used as the material and the integrated value in $^{29}$SiCP/MAS-NMR spectroscopy, the ratio between siloxane unit shown by Formula (1) and siloxane units shown by Formulas (2), (3), (4), (5) and (6) was calculated. The ratio between siloxane units shown by Formulas (2), (3) and (4) and siloxane units shown by Formulas (5) and (6) and the ratio between siloxane units shown by Formulas (3) and (5) and siloxane units shown by Formulas (4) and (6) were also similarly calculated.

Test Examples 2-10 and Comparison Examples 1-4

Synthesis of Organosilicon Fine Particles (P-2)-(P-10) and (R-1)-(R-4)

Organosilicon fine particles (P-2)-(P-10) and (R-1)-(R-4) were synthesized and analyzed as for organosilicon fine particles (P-1).

Test Example 11

Synthesis of Organosilicon Fine Particles (P-11)

Ion exchange water 700 g was placed inside a reactor and 48% aqueous solution of sodium hydroxide 0.6 g and 20% aqueous solution of 10-mol ethylene oxide adduct of nonylphenol 0.25 g were added and stirred to obtain a uniform aqueous solution. A monomer mixture with methyltrimethoxy silane 23.1 g (0.17 mol), 3-methacryloxypropyl trimethyl silane 57.1 g (0.23 mol) and tetraethoxy silane 125.0 g (0.6 mol) was dropped slowly while its temperature was maintained at 14° C. such that the aqueous solution and the mixed monomer would not become mixed and then stirred slowly such that each would stay in a condition of a laminar flow. After one hour, 10% aqueous solution of dodecylbenzene sodium sulfonate 3 g was added. After it was further stirred for 3 hours at the same temperature, it was matured for 5 hours at 30° C. to have an aqueous suspension generated. This aqueous suspension was passed through a membrane filter with hole diameter of 10 μm produced by Advantec Mfs, Inc. and a centrifuge was further employed to separate white fine particles. These white fine particles thus obtained were washed with water and dried with hot wind for 5 hours at 150° C. to obtain organosilicon fine particles (P-12) 71.3 g. Organosilicon fine particles (P-12) were similarly observed, measured and analyzed as done in Test Example 1.

Test Example 12

Synthesis of Organosilicon Fine Particles (P-12)

Organosilicon fine particles (P-12) were synthesized and analyzed as for organosilicon fine particles (P-11).

Test Example 13

Synthesis of Organosilicon Fine Particles (P-13)

Ion exchange water 700 g was placed inside a reactor and 48% aqueous solution of sodium hydroxide 0.6 g and 20% aqueous solution of 10-mol ethylene oxide adduct of nonylphenol 0.25 g were added and stirred to obtain a uniform aqueous solution. A monomer mixture with cyclohexyl trimethoxy silane 49.5 g (0.24 mol), 3-methacryloxypropyl trimethyl silane 89.4 g (0.36 mol) and tetraethoxy silane 83.3 g (0.4 mol) was dropped slowly while its temperature was maintained at 14° C. such that the aqueous solution and the mixed monomer would not become mixed and then stirred slowly for 4 hours such that each would stay in a condition of a laminar flow. An aqueous suspension was generated by maturing it for 5 hours at 30° C. This aqueous suspension was passed through a metallic net and a centrifuge was further employed to separate white fine particles. These white fine particles thus obtained were washed with water and dried with hot wind for 5 hours at 150° C. to obtain organosilicon fine particles (P-13) 96.8 g. Organosilicon fine particles (P-13) were similarly observed, measured and analyzed as done in Test Example 1.

Test Examples 14 and 15

Synthesis of Organosilicon Fine Particles (P-14) and (P-15)

Organosilicon fine particles (P-14) and (P-15) were synthesized and analyzed as for organosilicon fine particles (P-13).

Test Example 16

Synthesis of Organosilicon Fine Particles (P-16)

Organosilicon fine particles (P-16) were synthesized and analyzed as in Test Example 1 except 10% aqueous solution of dodecylbenzene sodium sulfonate was not added.

Comparison Example 5

Synthesis of Organosilicon Fine Particles (R-5)

Ion exchange water 3950 g and 28% ammonia water 50 g were placed inside a reactor and stirred for 10 minutes at room temperature to obtain a uniform ammonia water solution. Methyltrimethoxy silane 600 g (4.41 mol) was added to this ammonia water solution such that they would not become mixed together in a two-layer condition with a layer of methyltrimethoxy at the top and a layer of ammonia water solution at the bottom. This was slowly stirred while maintaining this two-layer condition to carry out hydrolysis and condensation reaction at the boundary surface between the two layers. As the reaction progressed, the reaction product precipitated slowly such that the lower layer became white and turbid while the top layer of methyltrimethoxy became thinner, disappearing finally in about 3 hours. After it was stirred for 3 hours under the same condition while the temperature was maintained at 50-60° C., it was cooled to 25° C. and white fine particles which became precipitated like a suspension were filtered out. These white fine particles were washed with water and dried with hot wind for 3 hours at 150° C. to obtain organosilicon fine particles (R-5) 266 g. Organosilicon fine particles (R-5) thus obtained were similarly observed, measured and analyzed as done in Test Example 1.

Comparison Example 6

Synthesis of Organosilicon Fine Particles (R-6)

Ion exchange water 1080 g was placed inside a reactor and acetic acid 0.2 g was added to obtain a uniform solution. Methyltrimethoxy silane 1169.6 g (8.6 mol) and tetraethoxy silane 291.6 g (1.4 mol) were added to it to carry out a hydrolytic reaction while temperature was maintained at 30° C. A transparent reaction liquid containing silanol compound was obtained in about 30 minutes. Ion exchange water 475 g and dodecylbenzene sodium sulfonate 50 g were placed in another reactor and after it was sufficiently melted, temperature was maintained at 80-85° C. This transparent reaction liquid 300 g was dropped into this over about 2 hours to cause a condensation reaction. After it was matured for 15 minutes, it was slowly cooled and stirred for one hour until room temperature was reached. After the stirring, the pH value was adjusted to 7.0 by means of water solution of sodium carbonate to obtain an aqueous suspension and white fine particles were filtered out of this aqueous suspension. These white fine particles were washed with water and dried with hot wind for 3 hours at 150° C. to obtain organosilicon fine particles (R-6) 594 g. Organosilicon fine particles (R-6) thus obtained were similarly observed, measured and analyzed as done in Test Example 1.

Comparison Example 7

Synthesis of Organosilicon Fine Particles (R-7)

Ion exchange water 1080 g was placed inside a reactor and acetic acid 0.2 g was added to obtain a uniform solution. Methyltrimethoxy silane 816 g (6 mol) and tetraethoxy silane 832 g (4 mol) were added to it to carry out a hydrolytic reaction while temperature was maintained at 30° C. A transparent reaction liquid containing silanol compound was obtained in about 30 minutes. Ion exchange water 475 g and dodecylbenzene sodium sulfonate 50 g were placed in another reactor and after it was sufficiently melted, temperature was maintained at 80-85° C. This transparent reaction liquid 300 g was dropped into this over about 2 hours to cause a condensation reaction. After it was matured for 15 minutes, it was slowly cooled and stirred for one hour until room temperature was reached. After the stirring, the pH value was adjusted to 7.0 by means of water solution of sodium carbonate to obtain an aqueous suspension and white fine particles were filtered out of this aqueous suspension. These white fine particles were washed with water and dried with hot wind for 3 hours at 150° C. to obtain organosilicon fine particles (R-7) 578 g. Organosilicon fine particles (R-7) thus obtained were similarly observed, measured and analyzed as done in Test Example 1.

Comparison Example 8

Synthesis of Organosilicon Fine Particles (R-8)

Ion exchange water 700 g was placed inside a reactor and 48% aqueous solution of sodium hydroxide 0.2 g was added to obtain a solution. Methyltrimethoxy silane 81.6 g (0.6 mol) and tetraethoxy silane 83.2 g (0.4 mol) were added to it to carry out a hydrolytic reaction for 4 hours while temperature was maintained at 13-15° C. to obtain a transparent reaction liquid containing silanol compound. A condensation reaction was carried out by maintaining the temperature of this reaction liquid at 30-80° C. to obtain an aqueous suspension. This aqueous suspension was passed through a membrane filter with hole diameter of 10 μm produced by Advantec Mfs, Inc. and a centrifuge was further employed to separate white fine particles. These white fine particles thus obtained were washed with water and dried with hot wind for 5 hours at 150° C. to obtain organosilicon fine particles (R-8) 58 g. Organosilicon fine particles (R-8) were similarly observed, measured and analyzed as done in Test Example 1.

Comparison Example 9

Synthesis of Organosilicon Fine Particles (R-9)

Ion exchange water 100 g, acetic acid 0.02 g and 10% aqueous solution of dodecylbenzene sodium sulfonate 3 g were placed inside a reactor to obtain a uniform aqueous solution. Methyltrimethoxy silane 47.6 g (0.35 mol), 3-mercaptopropyl trimethoxy silane 9.8 g (0.05 mol), dimethyldimethoxy silane 24.0 g (0.20 mol) and tetraethoxy silane 72.9 g (0.35 mol) were added to this aqueous solution to carry out a hydrolytic reaction while temperature was maintained at 30° C. A transparent reaction liquid containing silanol compound was obtained in about 30 minutes. Ion exchange water 700 g was placed in another reactor and 48% aqueous solution of sodium hydroxide 0.3 g was added to obtain a uniform aqueous solution. The aforementioned transparent reaction liquid was gradually added to this aqueous solution to cause a condensation reaction for 5 hours by keeping the temperature at 13-15° C. and a further condensation reaction for 5 hours by keeping the temperature at 30-80° C. to obtain an aqueous suspension. A centrifuge was used on this aqueous suspension to separate white fine particles. These white fine particles were washed with water and dried with hot wind for 5 hours at 150° C. to obtain organosilicon fine particles (R-9) 59 g. Organosilicon fine particles (R-9) were similarly observed, measured and analyzed as done in Test Example 1.

Details of these organosilicon fine particles synthesized in these examples are summarized in Tables 1-3.

TABLE 1

| | Kind | (1)*1 Kind/Ratio | (2)*2 Kind/Ratio | (3)*3 Kind/Ratio | Molar ratio (1)/((2) + (3)) | Molar ratio (1)/(2) | Surfactant Kind/weight % |
|---|---|---|---|---|---|---|---|
| Test Example | | | | | | | |
| 1 | P-1 | E-1/40 | F-1/24 | G-1/36 | 40/60 | 40/60 | H-1/0.03 |
| 2 | P-2 | E-1/34 | F-1/23 | G-1/43 | 34/66 | 35/65 | H-1/0.01 |
| 3 | P-3 | E-1/50 | F-1/15 | G-1/35 | 50/50 | 30/70 | H-1/0.30 |
| 4 | P-4 | E-1/40 | F-1/30 | G-1/30 | 40/60 | 50/50 | H-1/0.03 |
| 5 | P-5 | E-1/28 | F-1/36 | G-1/36 | 28/72 | 50/50 | H-1/0.03 |
| 6 | P-6 | E-1/40 | F-1/14 | G-1/46 | 40/60 | 23/77 | H-1/0.03 |
| 7 | P-7 | E-1/40 | F-1/24 | G-2/36 | 40/60 | 40/60 | H-1/0.03 |
| 8 | P-8 | E-1/50 | F-1/25 | G-2/25 | 50/50 | 50/50 | H-1/0.03 |
| 9 | P-9 | E-2/50 | F-2/25 | G-3/25 | 50/50 | 50/50 | H-1/0.03 |
| 10 | P-10 | E-2/28 | F-3/24 | G-4/48 | 28/72 | 33/67 | H-1/0.03 |
| 11 | P-11 | E-1/58 | F-1/21 | G-1/21 | 58/42 | 50/50 | H-1/0.03 H-2/0.006 |
| 12 | P-12 | E-1/40 | F-1/24 | G-2/36 | 40/60 | 40/60 | H-1/0.03 H-2/0.006 |
| 13 | P-13 | E-2/40 | F-4/24 | G-1/36 | 40/60 | 40/60 | H-2/0.006 |
| 14 | P-14 | E-2/40 | F-5/24 | G-1/36 | 40/60 | 40/60 | H-2/0.006 |
| 15 | P-15 | E-1/40 | F-1/24 | G-2/36 | 40/60 | 40/60 | H-2/0.03 |
| 16 | P-16 | E-2/40 | F-6/24 | G-1/36 | 40/60 | 40/60 | — |
| Comparison Example | | | | | | | |
| 1 | R-1 | E-1/80 | F-1/12 | G-1/8 | 80/20 | 60/40 | H-1/0.03 |
| 2 | R-2 | E-1/80 | F-1/2 | G-1/18 | 80/20 | 10/90 | H-1/0.03 |
| 3 | R-3 | E-1/20 | F-1/36 | G-1/24 | 20/80 | 60/40 | H-1/0.03 |
| 4 | R-4 | E-1/20 | F-1/12 | G-1/68 | 20/80 | 15/85 | H-1/0.03 |
| 5 | R-5 | — | F-1/85 | G-4/15 | 0/100 | 85/15 | — |
| 6 | R-6 | E-1/14 | F-1/86 | — | 14/86 | 100/0 | — |
| 7 | R-7 | E-1/40 | F-1/60 | — | 40/60 | 100/0 | — |
| 8 | R-8 | E-1/40 | F-1/60 | — | 40/60 | 100/0 | H-1/0.03 |
| 9*4 | R-9 | E-1/35 | F-1/40 | G-1/5 | 44/56 | 89/11 | H-1/0.03 |

In Table 1:
Ratios are all in molar %;
*1 Silanol group forming silicide shown by Formula (7);
*2 Silanol group forming silicide shown by Formula (8);
*3 Silanol group forming silicide shown by Formula (9);
*4 Containing dimethyldimethoxy silane by 20 molar %;
E-1: Tetraethoxy silane;
E-2: Tetramethoxy silane;
F-1: Methyltrimethoxy silane;
F-2: Ethyltrimethoxy silane;
F-3: Propyltrimethoxy silane;
F-4: Cyclohexyltrimethoxy silane;
F-5: Phenyltrimethoxy silane;
F-6: Benzyltrimethoxy silane;
G-1: 3-methacryloxy propyltrimethoxy silane;
G-2: 3-acryloxy propyltrimethoxy silane;
G-3: 3-mercapto propyltrimethoxy silane;
G-4: Vinyltrimethoxy silane;
H-1: Sodium dodecylbenzene sulfonate;
H-2: 10 mol ethyleneoxide adduct of nonylphenol.

TABLE 2

| | Kind | (1)*5 Ratio | (2)*6 Ratio | (3)*7 Kind/Ratio | (4)*8 Kind/Ratio | (5)*9 Kind/Ratio | (6)*10 Kind/Ratio | *11 | *12 | *13 |
|---|---|---|---|---|---|---|---|---|---|---|
| Test Example | | | | | | | | | | |
| 1 | P-1 | 32.0 | 8.0 | A-1/19.2 | B-1/18.0 | C-1/4.8 | D-1/18.0 | 32/68 | 66/34 | 40/60 |
| 2 | P-2 | 27.0 | 7.0 | A-1/18.4 | B-1/21.5 | C-1/4.6 | D-1/21.5 | 27/73 | 64/36 | 35/65 |
| 3 | P-3 | 32.0 | 8.0 | A-1/13.5 | B-1/21.0 | C-1/4.5 | D-1/21.0 | 32/68 | 63/37 | 30/70 |
| 4 | P-4 | 32.0 | 8.0 | A-1/19.2 | B-1/15.0 | C-1/7.5 | D-1/15.0 | 32/68 | 66/34 | 50/50 |
| 5 | P-5 | 22.4 | 5.6 | A-1/19.2 | B-1/24.0 | C-1/4.8 | D-1/24.0 | 22/78 | 63/37 | 33/67 |
| 6 | P-6 | 32.0 | 8.0 | A-1/11.2 | B-1/23.0 | C-1/2.8 | D-1/23.0 | 32/68 | 62/38 | 23/77 |

TABLE 2-continued

|   | Kind | (1)*5 Ratio | (2)*6 Ratio | (3)*7 Kind/Ratio | (4)*8 Kind/Ratio | (5)*9 Kind/Ratio | (6)*10 Kind/Ratio | *11 | *12 | *13 |
|---|------|------|------|-----------|-----------|-----------|-----------|-------|-------|-------|
| 7 | P-7 | 32.0 | 8.0 | A-1/19.2 | B-2/16.0 | C-1/4.8 | D-2/20.0 | 32/68 | 64/36 | 40/60 |
| 8 | P-8 | 40.0 | 10.0 | A-1/20.0 | B-2/12.0 | C-1/5.0 | D-2/13.0 | 40/60 | 70/30 | 50/50 |
| 9 | P-9 | 40.0 | 10.0 | A-2/18.0 | B-3/10.0 | C-2/7.0 | D-3/15.0 | 40/60 | 61/39 | 50/50 |
| 10 | P-10 | 22.4 | 5.6 | A-3/19.2 | B-4/24.0 | C-3/4.8 | D-4/16.0 | 22/78 | 63/37 | 33/67 |
| 11 | P-11 | 46.4 | 11.6 | A-1/16.8 | B-1/11.0 | C-1/4.2 | D-1/10.0 | 46/54 | 73/27 | 50/50 |
| 12 | P-12 | 32.0 | 8.0 | A-1/19.0 | B-2/20.0 | C-1/5.0 | D-2/16.0 | 32/68 | 69/31 | 40/60 |
| 13 | P-13 | 32.0 | 8.0 | A-4/14.4 | B-1/18.0 | C-4/9.6 | D-1/18.0 | 32/68 | 59/41 | 40/60 |
| 14 | P-14 | 32.0 | 8.0 | A-5/12.2 | B-1/17.5 | C-5/10.8 | D-1/18.5 | 32/68 | 55/45 | 40/60 |
| 15 | P-15 | 32.0 | 8.0 | A-1/19.2 | B-2/19.0 | C-1/4.8 | D-2/17.0 | 32/68 | 68/32 | 40/60 |
| 16 | P-16 | 32.0 | 8.0 | A-6/10.2 | B-1/17.3 | C-6/12.0 | D-1/18.7 | 32/68 | 52/47 | 40/60 |
| Comparison Example | | | | | | | | | | |
| 1 | R-1 | 64.0 | 16.0 | A-1/9.6 | B-1/4.0 | C-1/2.4 | D-1/4.0 | 64/36 | 82/18 | 60/40 |
| 2 | R-2 | 64.0 | 16.0 | A-1/1.6 | B-1/9.0 | C-1/0.4 | D-1/9.0 | 64/36 | 74/26 | 10/90 |
| 3 | R-3 | 16.0 | 4.0 | A-1/28.8 | B-1/12.0 | C-1/7.2 | D-1/12.0 | 16/84 | 70/30 | 60/40 |
| 4 | R-4 | 16.0 | 4.0 | A-1/9.6 | B-1/34.0 | C-1/2.4 | D-1/34.0 | 16/84 | 57/43 | 15/85 |
| 5 | R-5 | — | — | A-1/68.0 | B-4/7.5 | C-1/17.0 | D-4/7.5 | 0/100 | 76/24 | 85/15 |
| 6 | R-6 | 12.0 | 2.0 | A-1/69.0 | — | C-1/17.0 | — | 12/88 | 81/19 | 100/0 |
| 7 | R-7 | 32.0 | 8.0 | A-1/48.0 | — | C-1/12.0 | — | 32/68 | 82/18 | 100/0 |
| 8 | R-8 | 32.0 | 8.0 | A-1/48.0 | — | C-1/12.0 | — | 32/68 | 82/18 | 100/0 |
| 9*14 | R-9 | 28.0 | 7.0 | A-1/32.0 | B-3/2.5 | C-1/8.0 | D-3/2.5 | 28/72 | 80/20 | 89/11 |

In Table 2:  
Ratios are all in molar %;  
*5 Siloxane unit shown by Formula (1);  
*6 Siloxane unit shown by Formula (2);  
*7 Siloxane unit shown by Formula (3);  
*8 Siloxane unit shown by Formula (4);  
*9 Siloxane unit shown by Formula (5);  
*10 Siloxane unit shown by Formula (6);  
*11 Molar ratio of (1)/((2) + (3) + (4) + (5) + (6));  
*12 Molar ratio of ((2) + (3) + (4))/((5) + (6));  
*13 Molar ratio of ((3) + (5))/((4) + (6));  
*14 Siloxane unit formed from dimethylmethoxy silane is contained by 20 molar %;  
A-1: Methylsiloxane unit;  
A-2: Ethylsiloxane unit;  
A-3: Propylsiloxane unit;  
A-4: Cyclohexylsiloxane unit;  
A-5: Phenylsiloxane unit;  
A-6: Benzylsiloxane unit;  
B-1: 3-methacyrloxypropylsiloxane unit;  
B-2: 3-acryloxypropylsiloxane unit;  
B-3: 3-mercaptopropylsiloxane unit;  
B-4: Vinylsiloxane unit;  
C-1: Hydroxymethylsiloxane unit;  
C-2: Hydroxyethylsiloxane unit;  
C-3: Hydroxypropylsiloxane unit;  
C-4: Hydroxycyclohexylsiloxane unit;  
C-5: Hydroxyphenylsiloxane unit;  
C-6: Hydroxybenzylsiloxane unit;  
D-1: Hydroxy-3-methacryloxypropylsiloxane unit;  
D-2: Hydroxy-3-acryloxypropylsiloxane unit;  
D-3: Hydroxy-3-mercaptopropylsiloxane unit;  
D-4: Hydroxyvinylsiloxane unit.

TABLE 3

|   | Kind | Shape | (1) Average outer diameter (μm) | (2) Average inner diameter (μm) | (3) Difference (1) − (2) (μm) |
|---|------|-------|------|------|------|
| Test Example | | | | | |
| 1 | P-1 | Ring shape | 3.0 | 2.2 | 0.8 |
| 2 | P-2 | Ring shape | 3.0 | 1.5 | 1.5 |
| 3 | P-3 | Ring shape | 1.2 | 0.6 | 0.6 |
| 4 | P-4 | Ring shape | 5.0 | 4.6 | 0.4 |
| 5 | P-5 | Ring shape | 0.5 | 0.3 | 0.2 |
| 6 | P-6 | Ring shape | 5.5 | 2.0 | 3.5 |
| 7 | P-7 | Ring shape | 7.0 | 4.8 | 2.2 |
| 8 | P-8 | Ring shape | 6.5 | 2.5 | 4.0 |
| 9 | P-9 | Ring shape | 1.2 | 0.8 | 0.4 |
| 10 | P-10 | Ring shape | 9.5 | 5.5 | 4.0 |
| 11 | P-11 | Ring shape | 3.0 | 2.8 | 0.2 |
| 12 | P-12 | Ring shape | 2.5 | 0.5 | 2.0 |
| 13 | P-13 | Ring shape | 13.2 | 8.8 | 4.4 |

TABLE 3-continued

|    | Kind | Shape | (1) Average outer diameter (μm) | (2) Average inner diameter (μm) | (3) Difference (1) − (2) (μm) |
|----|------|-------|---------------------------------|---------------------------------|-------------------------------|
| 14 | P-14 | Ring shape | 12.0 | 5.5 | 6.5 |
| 15 | P-15 | Ring shape | 3.0 | 2.3 | 0.7 |
| 16 | P-16 | Ring shape | 14.8 | 9.5 | 5.3 |
| Comparison Example | | | | | |
| 1 | R-1 | Indefinite | 3.7*[15] | | |
| 2 | R-2 | Indefinite | 4.9*[15] | | |
| 3 | R-3 | Indefinite | 16.0*[15] | | |
| 4 | R-4 | Indefinite | 18.0*[15] | | |
| 5 | R-5 | Solid sphere | 3.0*[15] | | |
| 6 | R-6 | Solid sphere with surface indentations | 2.6*[15] | | |
| 7 | R-7 | Sectionally horseshoe shape | 4.5*[15] | | |
| 8 | R-8 | Hollow Hemisphere | 6.5*[15] | | |
| 9 | R-9 | Rugby ball shape | *[16] | | |

In Table 3
*[15] Average particle diameter measured by laser diffraction/dispersion apparatus for measuring granularity distribution (Model LA-700 produced by Horiba Seisakusho);
*[16] Organic fine particles with shape of a rugby ball with average major axis of 16.0 μm and average minor axis of 7.0 μm as measured by observation of secondary electron image of electron microscope.

Part 2 (Evaluation as Polymer Modifier for Antireflection Film)

A mixture of organosilicon fine particles synthesized in Part 1 (10 parts), epoxy acrylate UV resin (with solid component 95%) (product name KR-566 produced by Asahi Denka Co., Ltd.) (90 parts) and methylisobutylketone (300 parts) was dispersed by means of a sand mill to obtain a paint liquid. After this liquid was applied to one surface of a transparent film of triacetyl cellulose (thickness 80 μm, transmissivity 92%) by the reverse coating method and dried for 2 minutes at 100° C., it was exposed to ultraviolet radiation by using a concentrating high pressure mercury light of 120 W/cm under the condition of radiation distance=10 cm and exposure time=30 seconds to harden the membrane on the transparent film and to obtain an antireflection film having an antireflection layer.

The transmission image visibility of the film thus prepared was measured according to JIS-K7105 by using a mapping measuring instrument (product name of ICM-1DP produced by Suga Test Instruments Co., Ltd.) in the transmission mode and under the condition of optical slit width=0.5 mm, and the results of the measurements were evaluated according to the following standards:

A: Transmission image visibility is 60 or greater;
B: Transmission image visibility is 40 or greater and less than 60;
C: Transmission image visibility is 35 or greater and less than 40; and
D: Transmission image visibility is less than 35.

The film thus prepared was exposed to an uncovered fluorescent light (8000 cd/cm$^2$) without any louver and the degree of fading of its reflected image was evaluated according to the following standards:

A: The contour of the fluorescent light is totally or hardly recognizable;
B: The contour of the fluorescent light is vaguely recognizable;
C: The fluorescent light is vague but its contour is recognizable; and
D: The contour of the fluorescent light is clearly recognizable.

The results of the evaluation is shown in Table 4.

TABLE 4

| | | Evaluation | |
|---|---|---|---|
| | Kind | Clearness of transmitted image | Antireflection characteristic |
| Test Example | | | |
| 17 | P-1 | A | A |
| 18 | P-2 | A | A |
| 19 | P-3 | A | A |
| 20 | P-4 | B | A |
| 21 | P-5 | B | A |
| 22 | P-6 | B | A |
| 23 | P-7 | A | A |
| 24 | P-8 | B | A |
| 25 | P-9 | B | A |
| 26 | P-10 | B | A |
| 27 | P-11 | B | A |
| 28 | P-12 | A | A |
| 29 | P-13 | B | A |
| 30 | P-14 | B | A |
| 31 | P-15 | A | A |
| 32 | P-16 | B | A |
| Comparison Example | | | |
| 10 | R-1 | D | D |
| 11 | R-2 | D | D |
| 12 | R-3 | D | D |
| 13 | R-4 | D | D |
| 14 | R-5 | D | B |
| 15 | R-6 | D | B |
| 16 | R-7 | C | D |
| 17 | R-8 | C | D |
| 18 | R-9 | D | C |

Part 3 (Evaluation as Polymer Modifier for Film with Adherence Resistance)

Polyethylene terephthalate with limiting viscosity 0.62 as measured inside orthochlorophenol at 25° C. completely free of organic filler was extruded by means of an extruder from the cap and made into an extruded film with thickness 152μ while electrostatic voltage was applied on a drum cooled to 40° C. It was then stretched by 3.6 times on a metallic roll heated to 93° C. to obtain a uniaxially drawn film. At a position immediately before this uniaxially drawn film reaches a tenter, a surface of this uniaxially drawn film was uniformly coated with an aqueous suspension of organosilicon fine particles synthesized in Part 1 from a coater head with three rolls. The amount of the organosilicon fine particles coated in this process was about 2.3 g per 1 m$^2$ of the uniaxially drawn film (this being an equivalent of about 0.0129 g per 1 m$^2$ in the case of the biaxially stretched film described below). Lastly, this uniaxially drawn film with one surface coated was led into the tenter to be stretched by 3.5 times in the transverse direction at 101° C. and thermally set for 6.3 seconds at 225° C. to obtain a polymer film with adherence resistance as a biaxially stretched film. The total time of heating after one of the surfaces of the film was coated was 11 seconds.

The adherence resistance and anti-slip of the synthetic polymer films thus prepared were evaluated as follows.

After an adhesive tape was attached to the coated surface of the synthetic polymer film prepared as described above, it was cut to widths of 20 mm and the 180-degree peeling force between the film and the adhesive tape was measured by means of a tensilon. The adherence resistance was evaluated according to the following standards. In addition, the coated surface of the film was rubbed by 200 times of reciprocating motion with a load of 500 g on a white cotton cloth soaked in water (inclusive of 200 g by the own weight of the friction-providing member and 300 g as an additional weight) by using a friction tester for the color fastness test II described in JIS L0823 and the peeling force was measured similarly thereon and the durability of the adherence resistance was evaluated according to the following standards:

A: Peeling force is less than 10 g/20 mm (excellent);
B: Peeling force is 10 g/20 mm or greater and less than 50 g/20 mm (good);
C: Peeling force is 50 g/20 mm or greater and less than 70 g/20 mm (somewhat inferior); and
D: Peeling force is 70 g/20 mm or greater (inferior).

For anti-slip, after the synthetic polymer film with adherence resistance was adjusted for humidity for 24 hours under a condition of relative humidity of 65% and temperature 20° C., a friction tester (Model TR produced by Toyo Seiki Seisakusho, Ltd.) was used to measure coefficient of static friction according to ASTM-D-1894 and the measured value was evaluated according to the following standards:

A: 0.40 or greater and less than 0.70 (excellent anti-slip);
B: 0.30 or greater and less than 0.40 (good anti-slip);
C: 0.20 or greater and less than 0.30 (somewhat inferior anti-slip); and
D: Less than 0.20 (very inferior anti-slip and impractical).

These results of evaluation are shown together in Table 5.

TABLE 5

| | Kind | Evaluation | | |
| --- | --- | --- | --- | --- |
| | | Adherence resistance | Durability in adherence resistance | Anti-slip |
| Test Example | | | | |
| 33 | P-1 | A | A | A |
| 34 | P-2 | A | A | A |
| 35 | P-3 | A | A | A |
| 36 | P-4 | A | B | A |
| 37 | P-5 | A | B | A |
| 38 | P-6 | A | B | A |
| 39 | P-7 | A | A | A |
| 40 | P-8 | A | B | A |
| 41 | P-9 | A | B | A |
| 42 | P-10 | B | B | B |
| 43 | P-11 | A | B | A |
| 44 | P-12 | A | A | A |
| 45 | P-13 | A | B | B |
| 46 | P-14 | A | B | B |
| 47 | P-15 | A | A | A |
| 48 | P-16 | B | B | B |
| Comparison Example | | | | |
| 19 | R-1 | B | D | D |
| 20 | R-2 | B | D | D |
| 21 | R-3 | B | D | D |
| 22 | R-4 | B | D | D |
| 23 | R-5 | B | D | D |
| 24 | R-6 | B | D | D |
| 25 | R-7 | B | D | C |
| 26 | R-8 | B | C | D |
| 27 | R-9 | B | D | D |

Part 4 Evaluation as Cosmetic Material

For evaluation as skin care foundation material, organosilicon fine particles synthesized in Part 1 5 parts, titanium oxide 10 parts, kaoline 35 parts, talc 20 parts, fluid paraffin 10 parts, octamethylcyclotetrasiloxane 2 parts, isopropyl palmitate 6 parts and glycerol 3 parts were mixed uniformly and press-molded to prepare a foundation. This foundation was used in a sensory test by 30 panel members to have adherence and slip evaluated according to the following standards:

A: Excellent;
B: Good;
C: Somewhat inferior; and
D: Inferior.

The results are shown in Table 6.

TABLE 6

| | Kind | Evaluation | |
| --- | --- | --- | --- |
| | | Adherence resistance | Slip |
| Test Example | | | |
| 49 | P-1 | A | A |
| 50 | P-2 | A | A |
| 51 | P-3 | A | A |
| 52 | P-4 | A | B |
| 53 | P-5 | A | B |
| 54 | P-6 | A | B |
| 55 | P-7 | A | A |
| 56 | P-8 | A | B |
| 57 | P-9 | A | B |
| 58 | P-10 | B | B |
| 59 | P-11 | A | B |
| 60 | P-12 | A | A |
| 61 | P-13 | A | B |
| 62 | P-14 | A | B |
| 63 | P-15 | A | A |
| 64 | P-16 | B | B |
| Comparison Example | | | |
| 28 | R-1 | D | C |
| 29 | R-2 | D | C |
| 30 | R-3 | D | C |
| 31 | R-4 | D | C |
| 32 | R-5 | D | B |
| 33 | R-6 | C | B |
| 34 | R-7 | C | B |
| 35 | R-8 | C | B |
| 36 | R-9 | D | B |

What is claimed is:

1. Organosilicon fine particles comprising polysiloxane network structure having a circular ring shape as a whole, having an average outer diameter of 0.05-15 μm and an average inner diameter of 0.01-10 μm, wherein the difference between said average outer diameter and said average inner diameter is in the range of 0.04-5 μm;

wherein said polysiloxane network structure comprises siloxane units given respectively by formulas (1), (2), (3), (4), (5) and (6) shown below:

$$SiO_{4/2} \quad \text{formula (1)}$$

$$Si(OH)O_{3/2} \quad \text{formula (2)}$$

$$R^1SiO_{3/2} \quad \text{formula (3)}$$

$$R^2SiO_{3/2} \quad \text{formula (4)}$$

$$R^3Si(OH)O_{2/2} \quad \text{formula (5)}$$

$$R^4Si(OH)O_{2/2} \quad \text{formula (6)}$$

where $R^1$ and $R^3$ are each nonreactive hydrocarbon group and $R^2$ and $R^4$ are each organic group having reactive group selected from the group consisting of acryloxy group, methacryloxy group, vinyl group and mercapto group; and wherein the molar ratio of (siloxane unit shown by formula (1))/(siloxane units shown by formulas (2), (3), (4), (5) and (6)) is 20/80-50/50, the molar ratio of (siloxane units shown by formulas (2), (3) and (4))/(siloxane units shown by formulas (5) and (6)) is 50/50-75/25, and the molar ratio of (siloxane units shown by formulas (3) and (5))/(siloxane units shown by formulas (4) and (6)) is 20/80-60/40.

2. The organosilicon fine particles of claim 1 wherein said average outer diameter is 0.1-8 μm, said average inner diameter is 0.05-6 μm, and the difference between said average outer diameter and said average inner diameter is in the range of 0.5-3 μm.

3. The organosilicon fine particles of claim 1 wherein $R^1$ is methyl group.

4. A method of producing the organosilicon fine particles of claim 1, said method comprising the steps of:

using silanol group forming silicides given respectively by formulas (7), (8) and (9) shown below:

$$SiX_4 \quad \text{formula (7)}$$

$$R^5SiY_3 \quad \text{formula (8)}$$

$$R^6SiZ_3 \quad \text{formula (9)}$$

where $R^5$ is nonreactive hydrocarbon group, $R^6$ is organic group having reactive group selected from the group consisting of acryloxy group, methacryloxy group, vinyl group and mercapto group, and X, Y and Z are each alkoxy group with 1-4 carbon atoms, alkoxyethoxy group having alkoxy group with 1-4 carbon atoms, acyloxy group with 2-4 carbon atoms, N,N-dialkylamino group having alkyl group with 1-4 carbon atoms, hydroxyl group, halogen atom or hydrogen atom, said silanol group forming silicides being used such that molar ratio of (silanol group forming silicide of formula (7))/((silanol group forming silicide of formula (8))+(silanol group forming silicide of formula (9))=25/75-60/40 and molar ratio of (silanol group forming silicide of formula (8))/(silanol group forming silicide of formula (9))=20/80-60/40;

generating silanol compounds by causing said silanol group forming silicides to contact with water in the presence of a catalyst and to thereby undergo hydrolysis; and causing a condensation reaction of said silanol compounds to thereby generate said organosilicon fine particles comprising polysiloxane network structure.

5. The method of claim 4 wherein $R^5$ is methyl group.

6. The method of claim 4 further comprising the step of fractionating said silanol compounds by a membrane filter after said condensation reaction.

7. The method of claim 4 wherein said silanol group forming silicides are caused to contact with water in the presence of said catalyst and also in the presence of at nonionic surfactants and anionic surfactants.

8. A method of providing a synthetic film or sheet with antireflection characteristic, said method comprising the step of causing the organosilicon fine particles of claim 1 to adhere to a surface of said synthetic film or sheet, wherein said synthetic film or sheet acquires antireflection characteristic.

9. A method of providing a synthetic film or sheet with antiblocking characteristic, said method comprising the step of causing the organosilicon fine particles of claim 1 to be present in said synthetic film or sheet, wherein said synthetic film or sheet acquires antiblocking characteristic.

10. A method of providing a skin care cosmetic material with adherence and slip characteristics, said method comprising the step of causing the organosilicon fine particles of claim 1 to be contained in said synthetic film or sheet, wherein said skin care cosmetic material acquires adherence and slip characteristics.

* * * * *